(12) United States Patent
Kawashima

(10) Patent No.: US 7,488,287 B2
(45) Date of Patent: Feb. 10, 2009

(54) ULTRASONIC DIAGNOSING SYSTEM

(75) Inventor: Tomonao Kawashima, Hachioji (JP)

(73) Assignee: Olympus Corporation, Tokyo (JP)

( * ) Notice: Subject to any disclaimer, the term of this patent is extended or adjusted under 35 U.S.C. 154(b) by 519 days.

(21) Appl. No.: 10/514,807

(22) PCT Filed: Sep. 12, 2003

(86) PCT No.: PCT/JP03/11692

§ 371 (c)(1),
(2), (4) Date: Nov. 12, 2004

(87) PCT Pub. No.: WO2004/028373

PCT Pub. Date: Apr. 8, 2004

(65) Prior Publication Data

US 2005/0228275 A1 Oct. 13, 2005

(30) Foreign Application Priority Data

Sep. 27, 2002 (JP) ............................ 2002-283804

(51) Int. Cl.
A61B 8/00 (2006.01)
(52) U.S. Cl. .................... 600/443; 600/447; 600/463
(58) Field of Classification Search ......... 600/443–448, 600/466, 463, 309, 437, 424; 382/131, 128; 128/916, 662
See application file for complete search history.

(56) References Cited

U.S. PATENT DOCUMENTS 4,821,731 A * 4/1989 Martinelli et al. ........... 600/463
5,724,978 A   3/1998 Tenhoff
5,771,895 A * 6/1998 Slager ....................... 600/462
5,830,145 A * 11/1998 Tenhoff ..................... 600/463
6,148,095 A * 11/2000 Prause et al. ............... 382/131
6,240,312 B1 * 5/2001 Alfano et al. ............... 600/476
6,248,074 B1   6/2001 Ohno et al.
6,456,735 B1 * 9/2002 Sato et al. .................. 382/131
6,477,401 B1 * 11/2002 Johnson et al. ............. 600/431

(Continued)

FOREIGN PATENT DOCUMENTS

JP          11-113913          4/1999

(Continued)

OTHER PUBLICATIONS

Supplementary European Search Report, to European Patent Application No. 03798403.6-1526 PCT/JP0311692, dated Aug. 17, 2007 (4 pgs.).

(Continued)

Primary Examiner—Eric F Winakur
Assistant Examiner—Lawrence N Laryea
(74) Attorney, Agent, or Firm—Straub and Pokotylo; John C. Pokotylo

(57) ABSTRACT

An ultrasonic diagnostic apparatus has an ultrasonic endoscope, an ultrasonic observing portion, a position detecting unit, a monitor, a keyboard, and a mouse. Cross-sectional planes in parallel therewith are set to radial tomographic images, an intersecting line segment is obtained between a radial tomographic image and the cross-sectional plane, the intersecting line segments are combined, and a route tomographic image is generated. It is easily recognized how the lesion is spreading along the luminal portion during the examination by advancing and returning a radial scanning ultrasonic probe. Further, which part in the luminal portion is scanning during the examination can easily be recognized during the examination.

20 Claims, 12 Drawing Sheets

U.S. PATENT DOCUMENTS

| | | | |
|---|---|---|---|
| 6,685,644 B2 * | 2/2004 | Seo et al. | 600/447 |
| 6,718,193 B2 * | 4/2004 | Knoplioch et al. | 600/407 |
| 2003/0020810 A1 * | 1/2003 | Takizawa et al. | 348/68 |
| 2003/0073935 A1 * | 4/2003 | Segawa et al. | 600/593 |
| 2003/0187369 A1 * | 10/2003 | Lewis et al. | 600/587 |

FOREIGN PATENT DOCUMENTS

| | | |
|---|---|---|
| JP | 11-318884 | 11/1999 |
| JP | 11 318904 | 11/1999 |
| JP | 2000-023980 | 1/2000 |
| JP | 2000-242766 | 9/2000 |
| JP | 2001-017430 | 1/2001 |
| JP | 2002-143167 | 5/2002 |
| JP | 2002-159472 | 6/2002 |

OTHER PUBLICATIONS

Prager, R. W. et al., "Stradx: real-time acquisition and visualization of freehand three-dimensional ultrasound," *Medical Image Analysis,* vol. 3, No. 2, pp. 129-140, (1998, OxfordUniversity Press, Oxford, GB).

* cited by examiner

ULTRASONIC DIAGNOSING SYSTEM

TECHNICAL FIELD

The present invention relates to an ultrasonic diagnostic apparatus which generates a plurality of time-series radial tomographic images in the advancing and returning operation of a radial scanning ultrasonic vibrator in the body cavity of a subject.

BACKGROUND ART

Japanese Unexamined Patent Application Publication No. 11-113913 discloses an ultrasonic diagnostic apparatus which has a position detector at the edge thereof and easily obtains spatial ultrasonic image data along a route by advancing and returning a general radial scanning ultrasonic probe (including an ultrasonic endoscope with an optical observing window) along a bent or inflected luminal portion so as to obtain a plurality of ultrasonic tomographic images. Various expressing methods of the spatial ultrasonic image data are examined and Japanese Unexamined Patent Application Publication No. 11-113913 discloses the expressing method with an ultrasonic three-dimensional image or a plurality of cross-sectional images which are sectioned by planes in different directions.

Further, Japanese Unexamined Patent Application Publication Nos. 11-318884 and 2000-242766 disclose apparatuses which easily form cross-sectional images that are longitudinally sectioned by curved surfaces along an observation target such as the vein and the intestine from spatial image data and which display a guiding image indicating by which curved surface the cross-sectional image is longitudinally sectioned.

The apparatuses disclosed in Japanese Unexamined Patent Application Publication Nos. 11-318884 and 2000-243766 have view-point setting means in the observation target included in the original image, which display a tomographic image obtained by longitudinally sectioning the image by the curved surface passing through a plurality of view points.

However, in the apparatus disclosed in Japanese Unexamined Patent Application Publication No. 11-113913, the spatial ultrasonic image data is expressed as the tomographic image obtained by sectioning the image data by a certain plane and then, the luminal portion is expressed as piecemeal images as shown in FIG. 14 and the entire luminal portion is not displayed on the screen in many cases. Because the luminal portion in the living body does not run on the specific plane. FIG. 14 shows a state of the luminal portion which partly runs on the depth side from the cross section.

Consequently, the apparatus disclosed in Japanese Unexamined Patent Application Publication No. 11-113913 has the following problems.

First problem: it is hard to clarify how the lesion is spreading along the luminal portion.

Second problem: it is hard to clarify which part in the luminal portion is scanning during the examination.

In the apparatuses disclosed in Japanese Unexamined Patent Application Publication Nos. 11-318884 and 2000-243766, the view point upon drawing the curved surface is set after the examination, that is, after obtaining all the original images necessary for continuous viewing of the luminal portion.

Therefore, the first problem is solved after the examination. However, the apparatuses disclosed in Japanese Unexamined Patent Application Publication Nos. 11-318884 and 2000-243766 have a drawback that the first problem is not solved in real-time during the examination. Further, the apparatuses disclosed in Japanese Unexamined Patent Application Publication Nos. 11-318884 and 2000-243766 have a drawback that the second problem such that it is hard to clarify which part in the luminal portion is scanning during the examination (particularly, during the scanning) is still unsolved.

Incidentally, in the apparatuses disclosed in Japanese Unexamined Patent Application Publication Nos. 11-318884 and 2000-243766, it is not considered that the examination is performed by using an ultrasonic probe which is inserted in the luminal portion in the body cavity.

Upon using the radial scanning ultrasonic probe in the body cavity, generally, the following examining method is used. That is, in general, the lesion is found during the examination and an image thereof is recorded in view of the examination efficiency and the invasion to a subject and the ultrasonic probe is sooner removed as much as possible after approximate diagnosis.

However, in the apparatuses disclosed in Japanese Unexamined Patent Application Publication Nos. 11-318884 and 2000-243766, the first and second problems are not solved during the examination, therefore, the recording of the necessary image is not clearly recognized, and the advantage to easily express the tomographic image is not obtained.

The present invention is devised in consideration of the above-mentioned circumstances and it is an object of the present invention to provide an ultrasonic diagnostic apparatus which can recognize how the lesion is spreading along the luminal portion during the examination and which can easily recognize which part in the luminal portion is scanning during the examination by advancing and returning the radial scanning ultrasonic probe in the body cavity.

DISCLOSURE OF INVENTION

According to the present invention, an ultrasonic diagnostic apparatus advances and returns a radial scanning ultrasonic vibrator in the body cavity of a subject and generates a plurality of time-series radial tomographic images in accordance with the advance and return. The ultrasonic diagnostic apparatus includes positional information detecting means which detects positional information of the radial scanning ultrasonic vibrator upon obtaining the radial tomographic image, and route tomographic generating means which generates a route tomographic image along a route of the advance and return of the radial scanning ultrasonic vibrator based on the positional information obtained from the positional information detecting means and the plurality of the time-series radial tomographic images.

Other features and advantages of the present invention will be obvious by the following description.

BRIEF DESCRIPTION OF THE DRAWINGS

FIG. 1 is a structural diagram showing the structure of an ultrasonic diagnostic apparatus, FIG. 2 is a diagram showing the structure of an edge of an ultrasonic endoscope, FIG. 3 is a flowchart for explaining the processing flow of the ultrasonic diagnostic apparatus shown in FIG. 1, FIG. 4 is a first diagram for explaining the operation of the ultrasonic diagnostic apparatus shown in FIG. 1, FIG. 5 is a second diagram for explaining the operation of the ultrasonic diagnostic apparatus shown in FIG. 1, FIG. 6 is a third diagram for explaining the operation of the ultrasonic diagnostic apparatus shown in FIG. 1, FIG. 7 is a fourth diagram for explaining the operation of the ultrasonic diagnostic apparatus shown in FIG. 1, FIG. 8 is a fifth diagram for explaining the operation of the ultrasonic diagnostic apparatus shown in FIG. 1, FIG. 9 is a sixth diagram for explaining the operation of the ultrasonic diagnostic apparatus shown in FIG. 1, and FIG. 10 is a seventh diagram for explaining the operation of the ultrasonic diagnostic apparatus shown in FIG. 1.

FIG. 11 is a structural diagram showing the structure of an ultrasonic apparatus, and FIG. 12 is a diagram showing the structure of an edge of an ultrasonic endoscope shown in FIG. 11.

BEST MODE FOR CARRYING OUT THE INVENTION

A detailed description is given of the present invention with reference to the drawings.

First Embodiment

Hereinbelow, a description is given of the structure and the operation of an ultrasonic diagnostic apparatus according to the first embodiment with reference to FIGS. 1 to 10.

(Structure)

Figure 1:
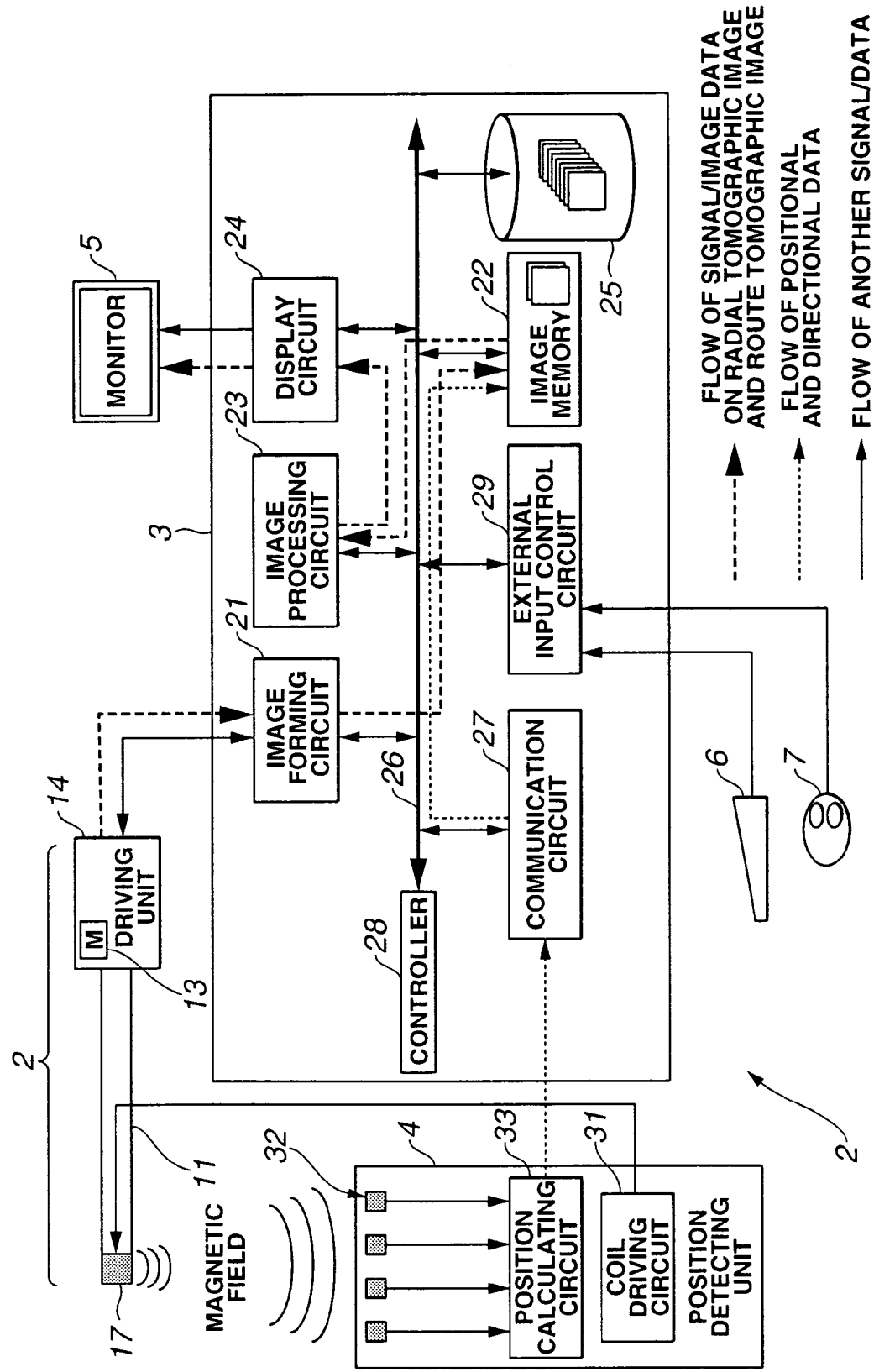
FIGS. 1 to 10 relate to the first embodiment of the present invention.

Referring to FIG. 1, an ultrasonic diagnostic apparatus 1 according to the first embodiment comprises an ultrasonic endoscope 2, an ultrasonic observing portion 3, a position detecting unit 4, a monitor 5, a keyboard 6, and a mouse 7.

The ultrasonic endoscope 2 has an inserting portion 11 which is inserted in the body cavity of a subject, containing a flexible material, and a driving unit 14 having a motor 13 for driving an ultrasonic vibrator (which will be described later) of the inserting portion edge.

Figure 2:
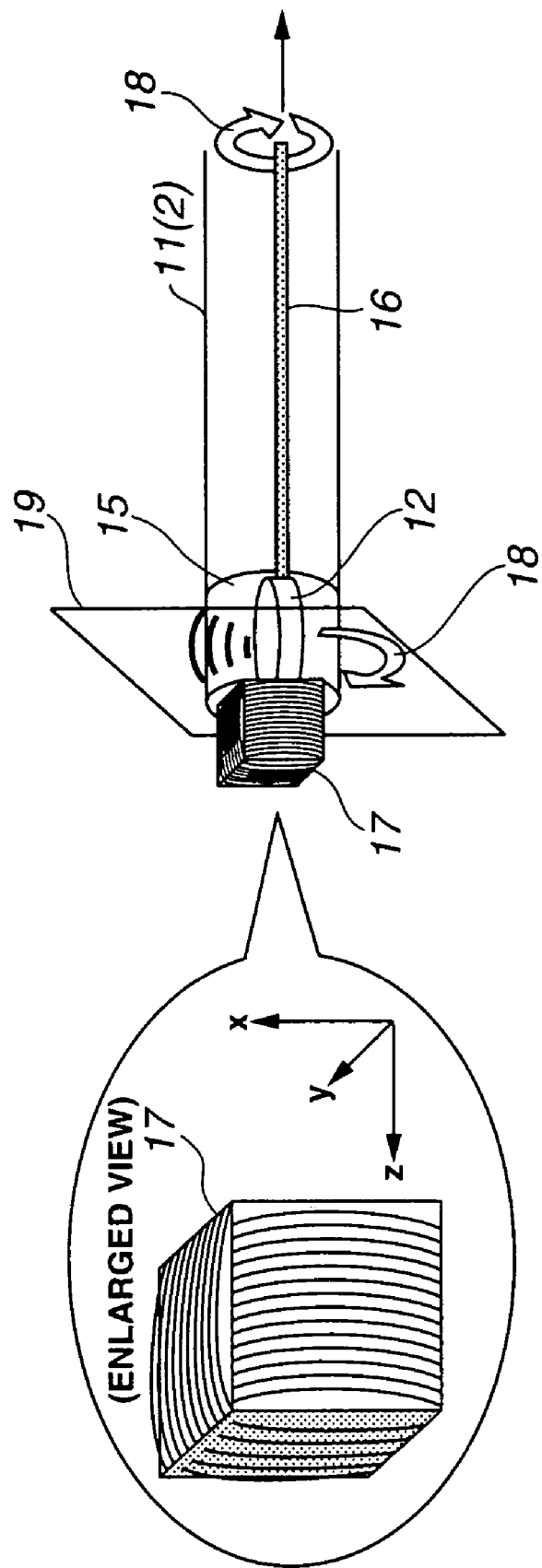

The state of the edge of the inserting portion 11 will be described with reference to FIG. 2. Referring to FIG. 2, the inserting portion 11 has, at the edge thereof, an acoustic transparent edge cap 15 which is made of a material for transmitting ultrasonic waves. The edge cap 15 has the ultrasonic vibrator 12, and the edge cap 15 is filled with a so-called acoustic medium (not shown). The ultrasonic vibrator 12 is connected to a flexible shaft 16 also made of a flexible material. The flexible shaft 16 is connected to the motor 13 in the driving unit 14.

The ultrasonic vibrator 12 is connected via a signal line (not shown) in the flexible shaft 16 to an image forming circuit (which will be described) in the ultrasonic observing portion 3 via the driving unit 14. The inserting portion 11 further has, at the edge thereof, a transmitting coil 17 with a magnetic filed in space. The transmitting coil 17 is connected to a coil driving circuit (which will be described later) in the position detecting unit 4 via a signal line. The transmitting coil 17 is wound with the axes in two perpendicular directions (y- and z-axes in FIG. 2). The z-axis is the inserting direction of the ultrasonic endoscope 2, and the y-axis is vertical to the z-axis and is in parallel of the radial scanning plane (which will be described later).

Referring back to FIG. 1, the ultrasonic observing portion 3 comprises: an image forming circuit 21 which outputs a pulse-voltage excitation signal to the ultrasonic vibrator 12, performs various receiving signal processing of an echo signal from the ultrasonic vibrator 12, and forms ultrasonic image data; an image memory 22 which stores a plurality of pieces of image data; an image processing circuit 23 which performs various imaging processing of the image data; a display circuit 24 which performs D/A conversion processing of the image data and which converts the image data into an analog video signal; a three-dimensional data recording unit 25 which comprises a rigid disk or a large-capacity memory; a communication circuit 27 which communicates with the position detecting unit 4 and supplies positional and directional data to a bus 26; and an external input control circuit 29 which transmits an input from the keyboard 6 and the mouse 7 to a controller 28. The bus 26 receives and transmits a control command and data to the above circuits and the above portions. The controller 28 outputs the control command to the above circuits via the bus 26.

The position detecting unit 4 comprises: a coil driving circuit 31 which outputs a coil excitation signal to the transmitting coil 17; a plurality of receiving coils (hereinafter, referred to as receiving coils) 32 which sequentially detect the magnetic field of the transmitting coil 17 and output electric receiving signals; and a position calculating circuit 33 which outputs positional and directional data from the receiving signal outputted from the receiving coils 32.

A thick broken line shown in FIG. 1 indicates the flow of signal/image data of a radial tomographic image (which will be described later) and a route tomographic image (which will be described later), and a thin broken line indicates the flow of positional and directional data.

(Operation)

Hereinbelow, the operation of the first embodiment will be described.

The operation for forming the radial tomographic image will be described.

The ultrasonic vibrator 12 receives a pulse-voltage excitation signal from the image forming circuit 21 in the ultrasonic observing portion 3 and converts the received signal into ultrasonic beams as coarse waves of a medium. The ultrasonic beams are transmitted to the acoustic medium and the edge cap 15, and are radiated to the outside of the ultrasonic endoscope 2. Further, a reflection echo from the subject traces a route inverse to that of the ultrasonic beams and returns to the ultrasonic vibrator 12. The ultrasonic vibrator 12 converts the reflecting echo into an electric echo signal and transmits the converted signal to the image forming circuit 21 with a route inverse to that of the excitation signal.

Furthermore, while repeating the operation, the motor 13 in the driving unit 14 is rotated, thereby rotating the flexible shaft 16 and the ultrasonic vibrator 12 in the direction shown by a block arrow 18 in FIG. 2. Thus, the ultrasonic beams are sequentially radiated radially in a plane (hereinlater, referred to as a radial scanning plane) 19 in FIG. 2 vertical to the inserting portion 11 in the ultrasonic endoscope 2 and, so-called mechanical radial scanning is realized (hereinafter, simply referred to as radial scanning).

The image forming circuit 21 performs the well-known processing of the echo signal from the ultrasonic vibrator 12, such as the envelop detection, logarithm amplification, A/D conversion, scanning conversion (processing for data on a converting polarity-coordinate system generated by the radial scanning into image data on an orthogonal-coordinate system), etc. Thus, the image forming circuit 21 forms the ultrasonic image data (hereinafter, referred to as the radial tomographic image). The radial tomographic image is outputted and is stored in the image memory 22 via the bus 26.

Next, the operation of the positional and directional data will be described.

The coil driving circuit 31 sequentially outputs the coil excitation signal to the transmitting coil 17. The transmitting coil 17 generates the magnetic coil in space. The receiving coils 32 sequentially detect the magnetic field and output electric receiving signals to the position calculating circuit 33. The position calculating circuit 33 calculates the positional and directional data based on the receiving signal and outputs the calculated data to the communication circuit 27 in the ultrasonic observing portion 3.

The positional and directional data contains data on the positions and directions of the receiving coils 32 in the transmitting coil 17. Specifically, the positional and directional data contains not only the position of the transmitting coil but also an inserting direction (z-axis in FIG. 2) of the ultrasonic endoscope and a specific direction in parallel with the radial tomographic image (y-axis FIG. 2). The transmitting coil 17 is attached so that the y-axis in FIG. 2 is in a 12 o'clock direction of the radial tomographic image (in the upper direction displayed on the monitor) and, then, the positional and directional data includes data on the normal-line direction of the radial tomographic image (z-axis in FIG. 2) and data on the 12 o'clock direction (y-axis in FIG. 2).

The communication circuit 27 outputs the positional and directional data to the bus 26. The positional and directional data is outputted and stored in the image memory 22 via the bus 26.

The controller 28 synchronizes the radial tomographic image to the positional and directional data, correlates them, and stores them.

Next, the operation for generating the route tomographic image will mainly be described.

First, the direction of the cross-sectional plane is set. An operator normally advances and returns the (radial scanning) ultrasonic endoscope 2 in the body cavity so as to sequentially obtain a plurality of radial tomographic images, thereafter, sections the images as spatial image data by the specific plane, and observes the cross-sectional image. What is referred to as the cross-sectional plane indicates the specific plane.

According to the features of the first embodiment, the cross-sectional planes which are in parallel therewith are set for the radial tomographic images, an intersecting line segment is obtained between the radial tomographic image and the cross-sectional plane, the intersecting line segments are combined, and thus the tomographic images (hereinafter, referred to as a route tomographic images) are generated.

Hereinbelow, a detailed description is given of the actual use of the ultrasonic diagnostic apparatus shown in FIG. 3 with reference to the flowchart.

Figure 3:
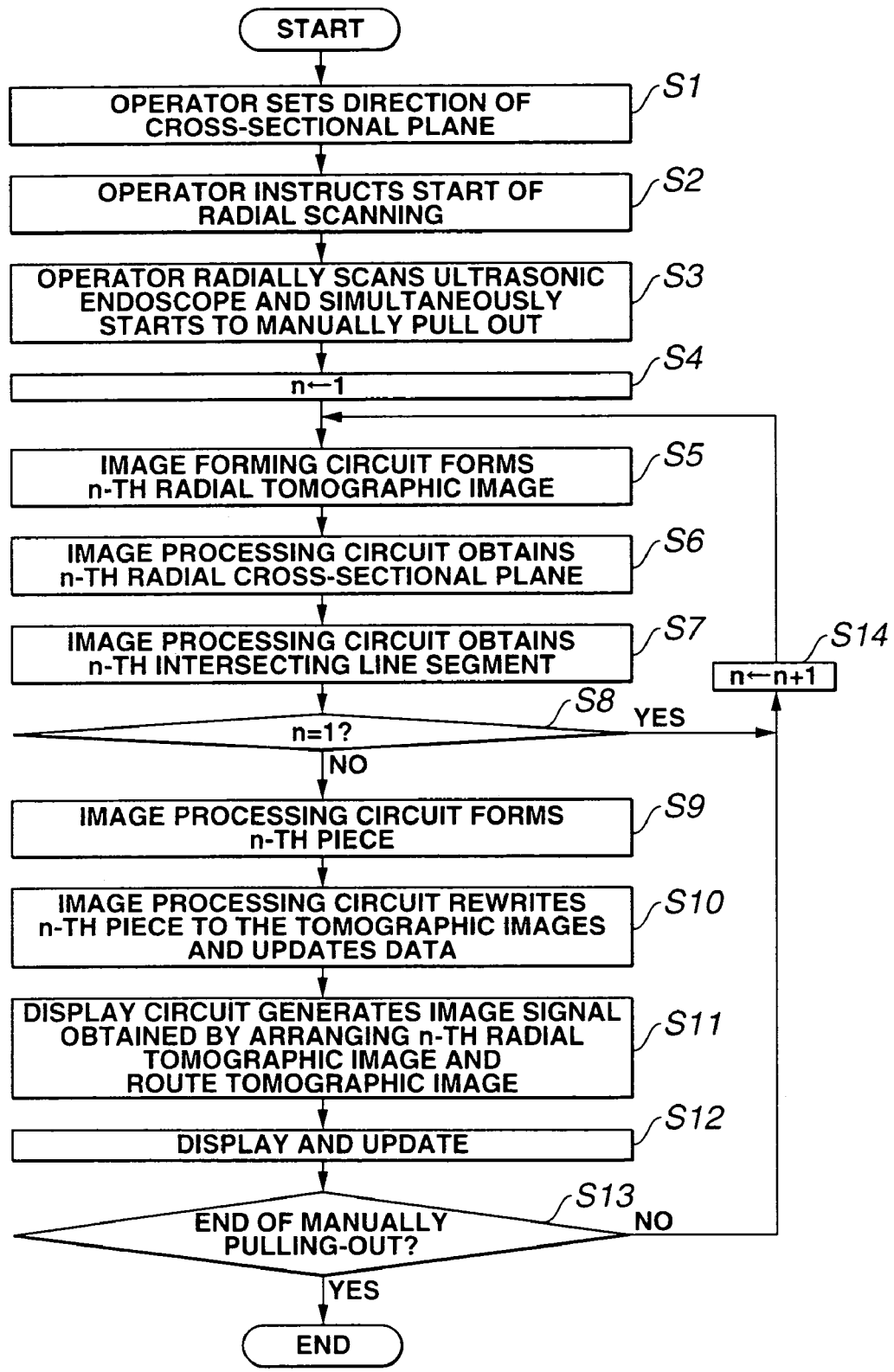

Referring to FIG. 3, in step S1, the operator sets the direction of the cross-sectional plane. Various setting methods are considered. Preferably, an arrow index for expressing the normal-line direction of the cross-sectional plane and a plate index for schematically expressing the cross-sectional plane are stereoscopically displayed on the monitor 5, the directions of the indexes are changed by the keyboard 6 or the mouse 7, and the directions of the cross-sectional planes are sensuously recognized.

In this case, preferably, the operator can further easily recognize and set a positional relationship between the ultrasonic endoscope 2 and the receiving coils 32 by stereoscopically displaying the indexes on the coordinate system based on the direction and the position of the ultrasonic endoscope 2 at the moment of the setting or based on the directions and the positions of the fixed receiving coils 32.

The specific operation is as follows. The operator inputs the direction of the cross-sectional plane from the keyboard 6 and the mouse 7. The information on the direction is transmitted to the controller 28 via the external input control circuit 29 and then is inputted to the image processing circuit 23 as a command from the controller 28. The image processing circuit 23 performs the image processing by using the positional and directional data so as to stereoscopically display the indexes, displays the data on the monitor 5 via the display circuit 24, and sets the directions of the cross-sectional planes.

In step S2, the operator instructs the start of radial scanning.

Specifically, the operator selects various menus by using a button (not shown) on the keyboard 6 or the mouse 7, then, the image forming circuit 21 outputs an excitation signal based on a command from the controller 28, and the radial scanning starts by rotating the motor 13.

In step S3, the operator radially scans the ultrasonic endoscope 2 that is inserted in the body cavity of the subject and simultaneously starts to insert and remove (hereinafter, referred to as "manually pull out) it along the luminal portion.

Figure 4:
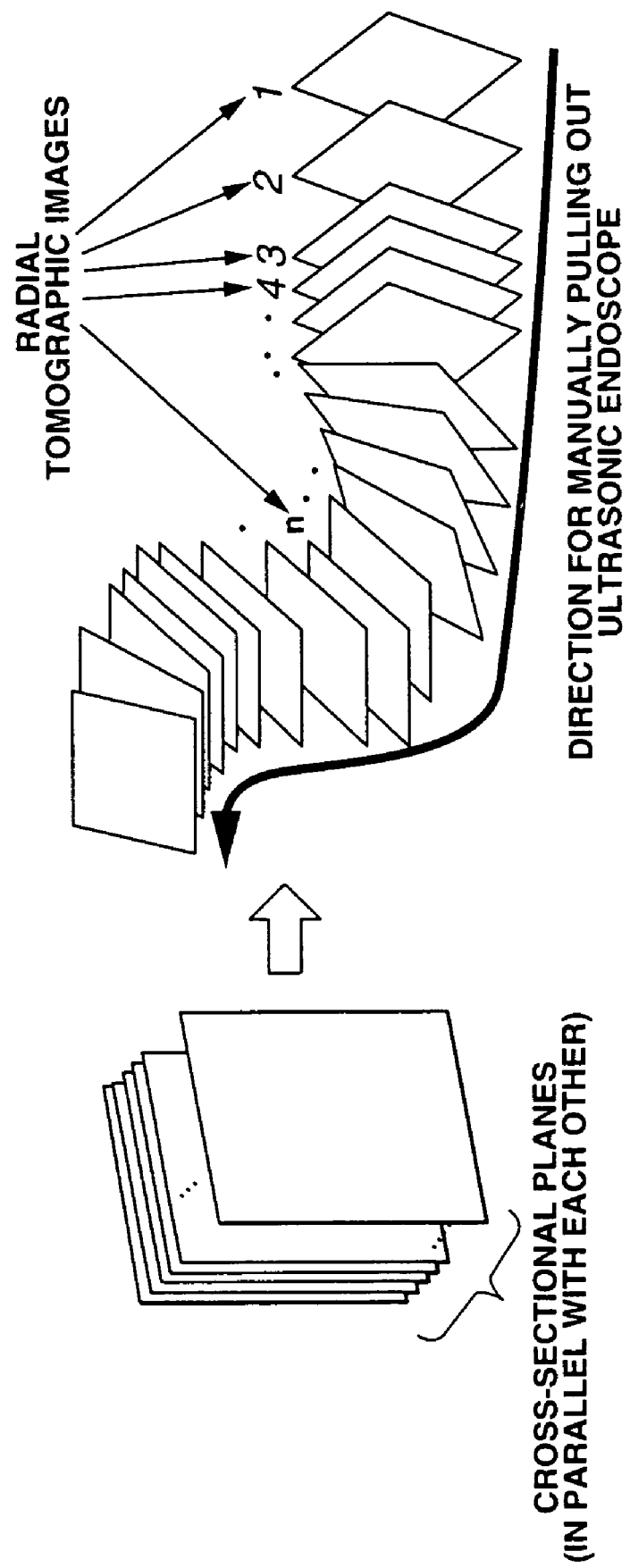

In the subsequent steps, the radial tomographic images are sequentially formed by repeating the radial scanning while pulling out the ultrasonic endoscope 2. This scanning method is referred to as "manually pulling-out and scanning". FIG. 4 shows the state of the "manually pulling-out and scanning". Referring to FIG. 4, the radial tomographic images are numbered starting from one in the forming order thereof.

In step S4, the image processing circuit 21 substitutes one for a variable n provided as a counter.

In step S5, the image forming circuit 21 forms an n-th radial tomographic image and the controller 28 synchronizes the radial tomographic image to the positional and directional data, correlates them, and stores the radial tomographic image and the positional and directional data.

In step S6, the image processing circuit 23 obtains the n-th radial cross-sectional plane. Specifically, the image processing circuit 23 reads, from the image memory 22, the n-th radial tomographic image and the positional and directional data correlated therewith, and the transmitting coil 17 is arranged near the ultrasonic vibrator 12. Consequently, the transmitting coil 17 is positioned in the rotating center of the ultrasonic vibrator 12 in the n-th radial tomographic image, and the n-th cross-sectional plane is obtained.

Figure 5:
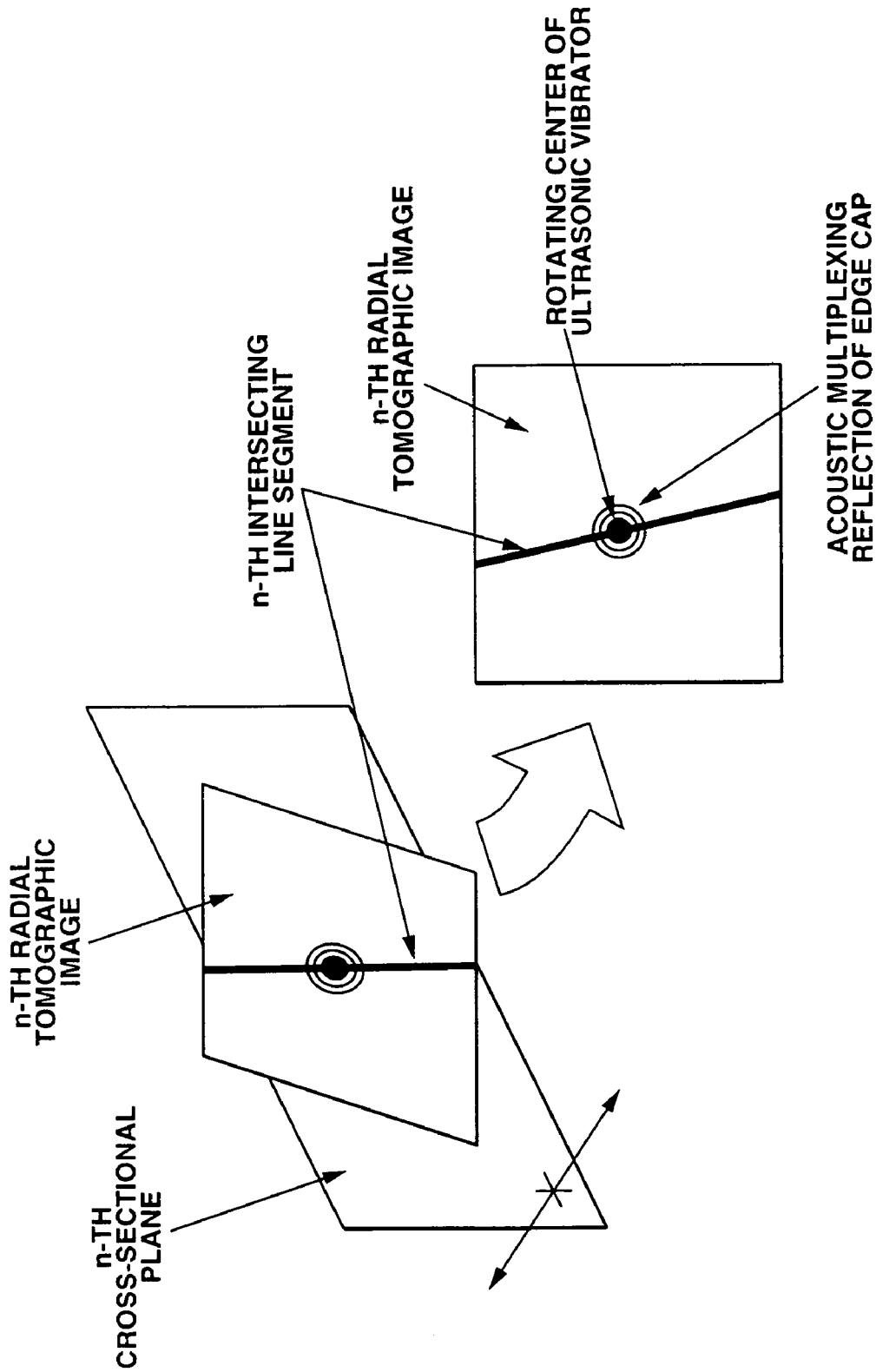

Hereinbelow, a detailed description is given of how to obtain the n-th cross-sectional plane. FIG. 5 shows the n-th cross-sectional plane. The n-th cross-sectional plane is in the direction set in step S1 and passes through the rotating center of the n-th radial tomographic image. The single cross-sectional plane is determined for the n-th radial tomographic image. Therefore, this step is repeated by changing the variable n, each single cross-sectional plane is obtained for each of the first, second, and . . . , radial tomographic images. All of the above-obtained cross-sectional planes for the first, second, and, . . . , radial tomographic images are in the direction set in step S1 and are in parallel therewith as shown in FIG. 4.

In step S7, the image processing circuit 23 obtains the intersecting line segment (n-th intersecting line segment) of the n-th radial tomographic image and the n-th cross-sectional plane. FIG. 5 shows the n-th intersecting line segment.

In step S8, in the case of n=1, the processing jumps to step S14.

Figure 6:
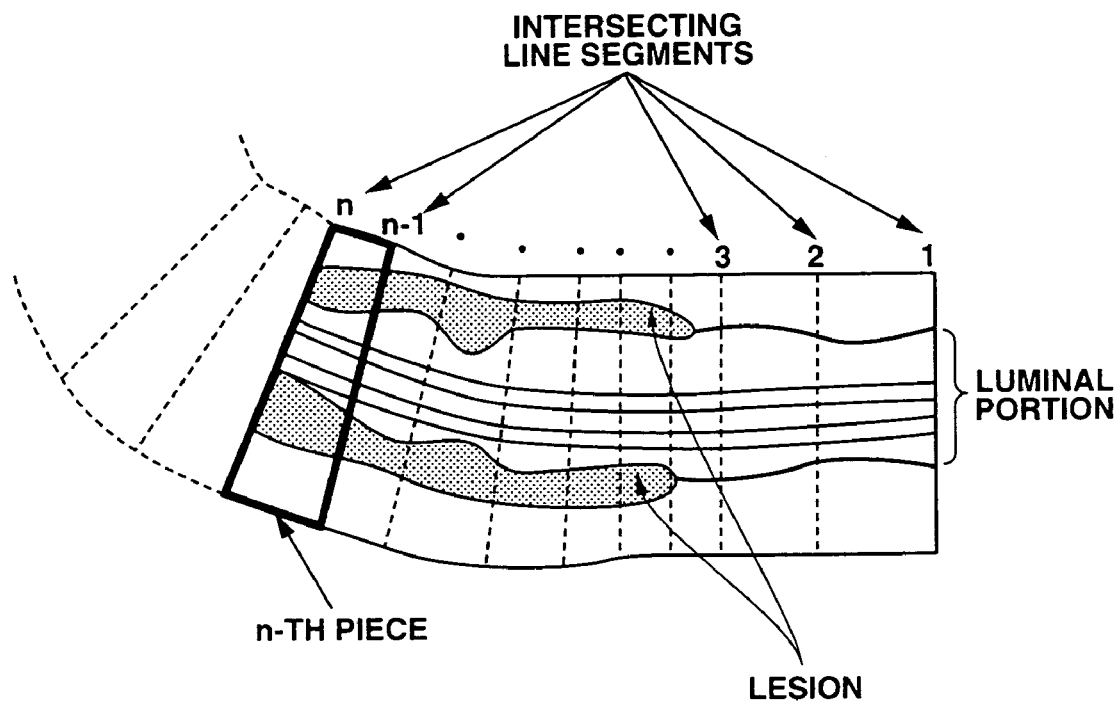

In step S9, the image processing circuit 23 interpolates image information on an (n−1)-th intersecting line segment and image information on the n-th intersecting line segment, and forms an n-th piece. FIG. 6 shows the n-th piece. Various interpolating methods are considered, for example, the interval between the intersecting lines is linearly interpolated and it is non-linearly interpolated along the route for manually pulling out.

Figure 7:
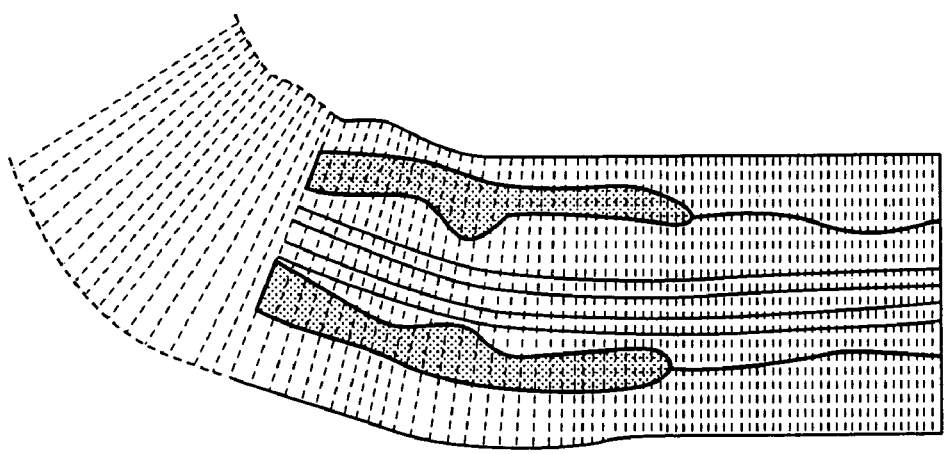

For the convenience of a description, the intersecting line segments are thinned out and drawn in FIG. 6 and, originally, the interval between the intersecting line segments are close to each other as shown in FIG. 7.

In step S10, the image processing circuit 23 rewrites the n-th piece to the previous route tomographic images and updates the images. That is, the image processing circuit 23 forms the new route tomographic image. FIG. 6 shows the updated route tomographic image.

Figure 8:
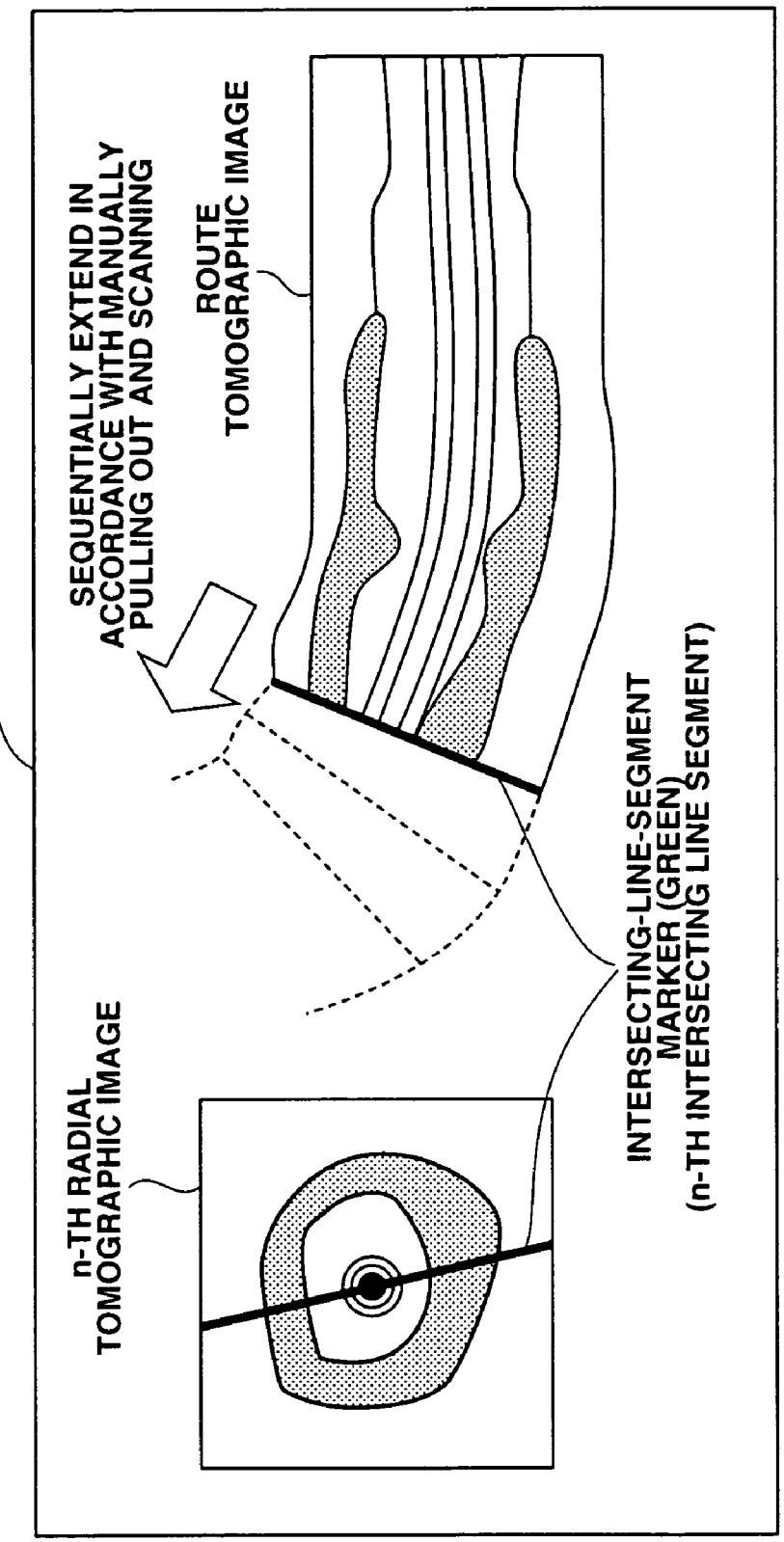

In step S11, the display circuit 24 generates an image signal obtained by arranging the n-th radial tomographic image and the route tomographic image. FIG. 8 shows the image in step S11. As shown in FIG. 8, the n-th radial tomographic image is on the left and the route tomographic image is on the right. Thick lines on the n-th radial tomographic image and on the route tomographic image are markers (hereinafter, referred to as intersecting-line-segment markers) indicating the intersecting line segment obtained for forming the route tomographic image. That is, the intersecting-line-segment maker shown in FIG. 8 indicates the n-th intersecting line segment and is displayed with a color different from that of the background such as green when the background image is a monochrome one.

In step S12, the monitor 5 arranges the n-th radial tomographic image and the route tomographic image and displays them.

The monitor 5 has displayed the (n−1)-th radial tomographic image and the route tomographic image obtained by superimposing the first to (n−1)-th pieces in the previous steps and, then, the screen is updated.

In step S13, the operator instructs the end of manually pulling-out and scanning via the keyboard 6 or the mouse 7. In other steps, the processing sequence jumps to step S14.

Specifically, the operator selects various menus by a button (not shown) on the keyboard 6 or the mouse 7 and instructs the end of manually pulling-out and scanning, then, the image forming circuit 21 stops the output of the excitation signal based on the command from the controller 28, the motor 13 stops rotating, and the radial scanning ends.

In step S14, the image processing circuit 23 increments the variable n provided as the counter by 1. After that, the image processing circuit 23 jumps the processing to step S5.

As mentioned above, unless the operator instructs the end of manually pulling-out and scanning, the processing from steps S5 to S14 is repeated.

By repeating the processing from steps S5 to S14, the route tomographic image is sequentially extended in accordance with the manually pulling-out and scanning as shown in FIG. 8.

According to the first embodiment, it is characterized that the image data comprising a plurality of radial tomographic images are not sectioned by the specific plane so as to generate the tomographic planar image, but a plurality of cross-sectional planes are obtained for a plurality of radial tomographic images, the radial tomographic images are sectioned by the cross-sectional planes, a plurality of intersecting line segments are obtained, the image data on the intersecting line segment is interpolated, the route tomographic image is generated on the two-dimensional screen.

The above description has been given of the operation for generating the route tomographic image during examination, especially, during the manually pulling-out and scanning. Hereinbelow, a description is given of the operation after the manually pulling-out and scanning.

The preparation needs the writing various data into the three-dimensional data recording unit 25 during the examination as preparation. Hereinbelow, a detailed description is given.

If the operator sets the direction of the cross-sectional plane in step S1, the controller 28 writes, to the three-dimensional data recording unit 25, a directional vector in the normal-line direction of the cross-sectional plane.

In step S6, when the image processing circuit 23 reads, from the image memory 22, the n-th radial tomographic image and the positional and directional data correlated therewith, the controller 28 correlates the n-th radial tomographic image with the positional and directional data, and writes the correlated result to the three-dimensional data recording unit 25.

With the above structure and operation, not only the operation described with reference to the flowchart shown in FIG. 3 is obtained during the manually pulling-out and scanning but also the cross-sectional planes and a plurality of continuous radial tomographic images are used after the manually pulling-out and scanning.

Next, the operation after the manually pulling-out and scanning will be described.

First, the controller 28 sequentially reads, to the image memory from the three-dimensional data recording unit 25, the radial tomographic image and the positional and directional data, starting from the first radial tomographic image.

In this case, the operator sets the cross-sectional plane similarly to the case in step S1, and the components perform the operation in steps S4 to S14. Consequently, the route tomographic image is obtained along the route for the manually pulling-out scanning upon obtaining the positional and directional data.

Figure 9:
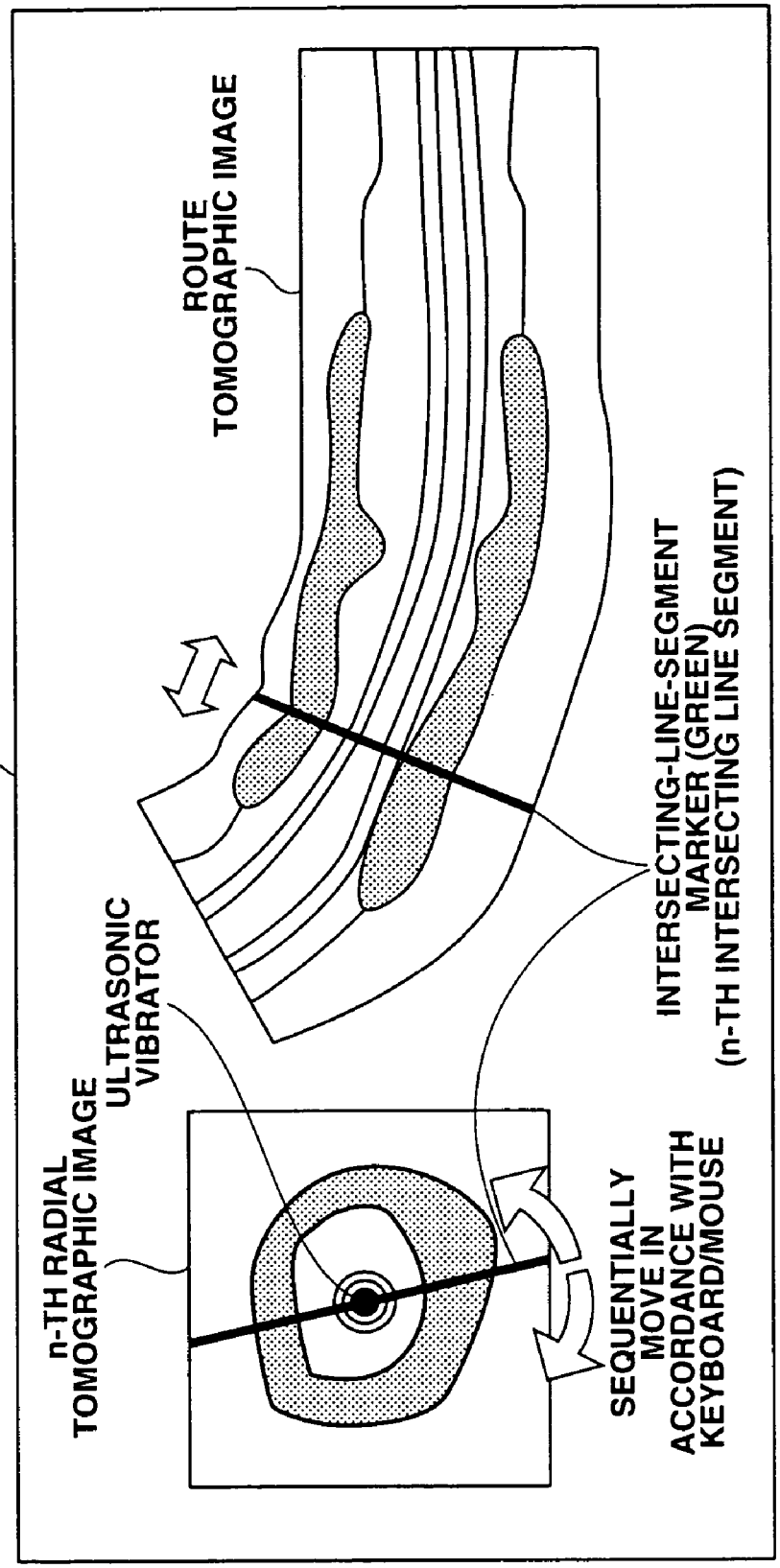

Further, referring to FIG. 9, the controller 28 changes the position and the direction of the intersecting line-segment marker on the route tomographic image and the intersecting-line-segment on the radial tomographic image based on the operator's instruction obtained via an arrow key (not shown) on the keyboard 6 or via the mouse 7.

The intersecting-line-segment marker on the route tomographic image can selectively be moved at the position of each intersecting line segment. For example, the intersecting-line-segment marker is in the direction shown by an arrow shown in FIG. 9.

The operator moves the intersecting-lie-segment marker, in accordance therewith, the (n−1)-th, n-th, (n+1)-th, . . . radial tomographic images are sequentially updated and are displayed on the left of the monitor 5.

The intersecting-lie-segment marker on the n-th radial tomographic image is rotated with the rotating center of the ultrasonic vibrator 12 as a center on the radial tomographic image. For example, the rotating direction is shown by an arrow in FIG. 9.

The operator rotates the intersecting-lie-segment marker, in accordance therewith, the cross-sectional plane is set again. Various methods for setting the new cross-sectional planes are considered. Hereinbelow, a detailed description is given.

For example, according to a first method, the new cross-sectional plane is vertical to the n-th radial tomographic image and passes through the intersecting-line-segment marker on the n-th radial tomographic image. In this case, although the original cross-sectional plane is not limited to be vertical to the n-th radial tomographic image, the operation of the keyboard 6 or the mouse 7 enables the cross-sectional plane to be set again to be vertical to the radial tomographic image as soon as the intersecting-line-segment marker starts to rotate on the radial tomographic image.

According to a second method, the new cross-sectional plane keeps an angle formed between the n-th radial tomographic image and the original cross-sectional plane (that is, an angle formed between the normal line of the n-th radial tomographic image and the normal line of the original cross-sectional plane), and passes through the intersecting-line-segment marker on the n-th radial tomographic image.

According to the first method, the cross-sectional plane is promptly set again vertically and thus the route tomographic image sharply changes. However, with the structure and the operation according to the second method, the sharp change can be prevented.

The operator rotates the intersecting-line-segment marker and, in accordance therewith, the new route tomographic image is sequentially updated and displayed on the right of the monitor 5.

A series of operations after the manually pulling-out and scanning is realized mainly by the operation of the image processing circuit 23 and the command from the controller 28.

The above description has given of the operation for generating the route tomographic image after the manually pulling-out and scanning. Hereinbelow, the operation for the new radial scanning after the manually pulling-out and scanning will be described.

First, the operator forms the route tomographic image and temporarily stops the radial scanning. After that, the operator performs the new radial scanning without removing the ultrasonic endoscope 2 from the subject. However, the route tomographic image is not updated in the new radial scanning.

Figure 10:
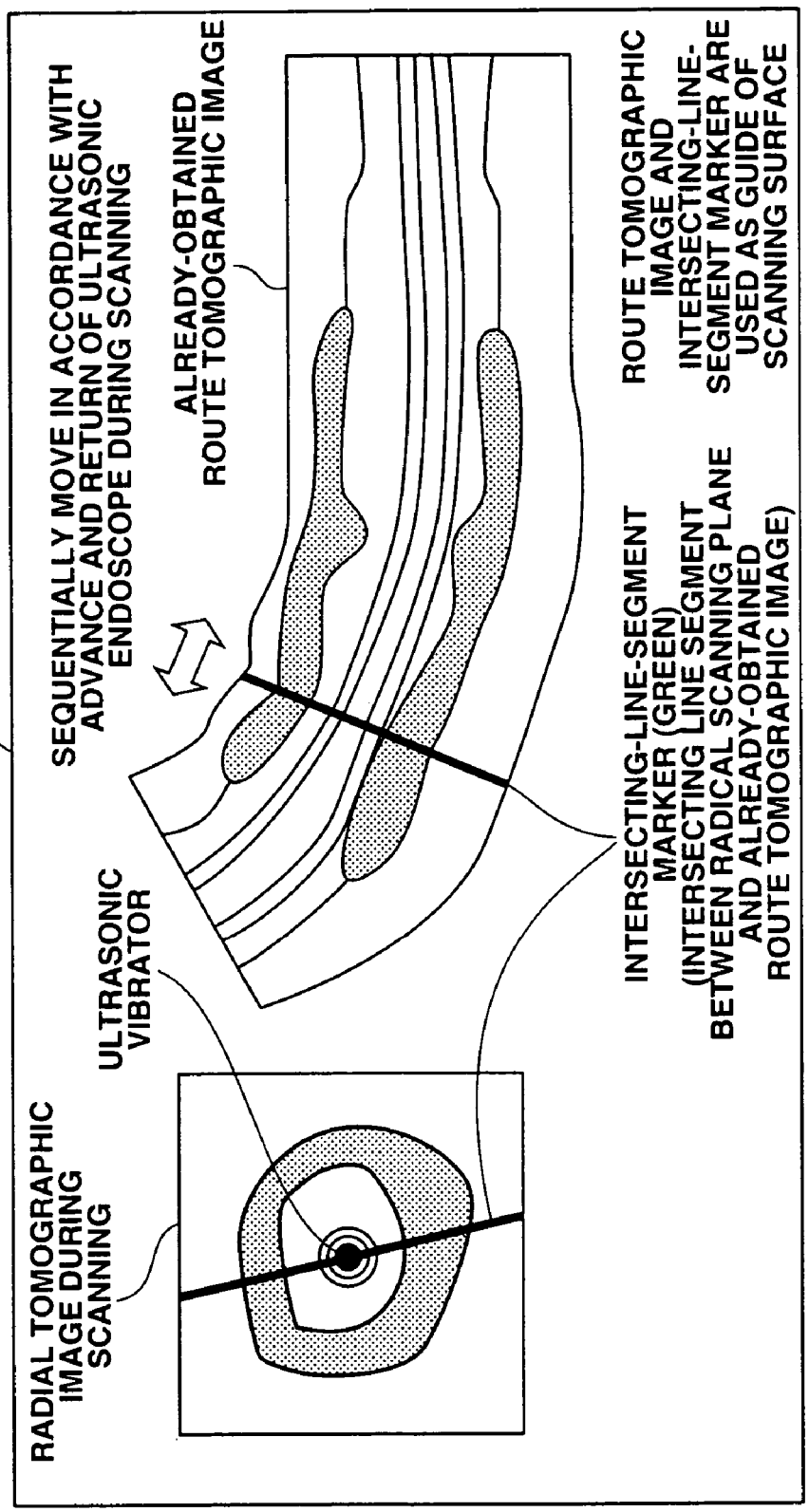

The image processing circuit 23 obtains the intersecting line segment of the already-obtained route tomographic image and the current radial scanning plane, generates the intersecting-line-segment marker based on the position of the intersecting line segment, superimposes the intersecting-line-segment marker on the obtained route tomographic image, and displays it. This state is shown in FIG. 10. In this case, the radial tomographic image which is currently scanned is displayed on the left of the screen on the monitor 5.

(Advantages)

With the structure and operations according to the first embodiment, the (radial scanning) ultrasonic endoscope 2 is advanced and returned in the body cavity. Thus, (1) how the lesion is spreading along the luminal portion during the examination is easily understood, and (2) which part of the luminal portion is scanning during the examination is easily understood.

Further, every formation of the radial tomographic image, the cross-sectional plane and the intersecting line segment are sequentially obtained, and the route tomographic image is updated and displayed. Consequently, the coordinate conversion of the two-dimensional image is not necessary, the scale of the image processing is reduced, and the route tomographic image is generated and updated fast irrespective of during or after the examination.

The intersecting-line-segment marker is provided so that the intersecting-line-segment is expressed between the radial tomographic image and the route tomographic image. Consequently, the positional relationship is easily understood irrespective of during/after the examination.

The intersecting-line-segment marker is moved on the route tomographic image by the input means such as the keyboard and the mouse and the radial tomographic image is updated in accordance with the movement. The route tomographic image is used as a guide for searching for the radial tomographic image. The obtained radial tomographic image is easily understood which part in the bent or inflected luminal portion is scanned. Therefore, the desired tomographic image is readily obtained and the interest area such as the lesion is easily drawn and found.

Further, the intersecting-line-segment line marker is moved little by little and the radial tomographic image is updated. Thus, the connection of the organ and the shape of the vas are easily understood and the spatial positional relationship is easily clarified between the lesion and the peripheral organ.

The intersecting-line-segment marker is rotated on the radial tomographic image by the input means such as the keyboard 6 or the mouse 7 and, in accordance therewith, the route tomographic image is updated. The desired route tomographic image is readily obtained, how lesion is spreading along the luminal portion is easily and precisely understood.

The image processing circuit 23 obtains the intersecting line segment between the already-obtained radial scanning plane and the route tomographic image, and generates the intersecting-line-segment marker based on the position of the intersecting line segment. The intersecting-line-segment marker is superimposed and displayed onto the obtained route tomographic image. The operator uses the route tomographic image and the intersecting-line-segment marker as the guide of the current radial scanning plane, and the lesion is easily drawn.

(Modification)

According to the first embodiment, the intersecting-line-segment marker is moved on the route tomographic image as shown in FIG. 8 and the radial tomographic image is updated. The intersecting-line-segment marker may be fixed and the route tomographic image may be scrolled.

During the manually pulling-out and scanning, the route tomographic image is out of the monitor screen and the route tomographic image may be scrolled so that the newest intersecting line segment is always displayed on the screen. With the above-described structure and operation, the operator easily understands which part in the living body is scanning by checking the screen.

According to the first embodiment, the intersecting-line-segment marker is rotated on the radial tomographic image and the route tomographic image is updated. However, the intersecting-line-segment marker may be fixed and the radial tomographic image may be rotated.

According to the first embodiment, the manually pulling-out and scanning is performed by pulling out the ultrasonic endoscope. On the contrary, the ultrasonic endoscope may be moved in the direction for inserting the ultrasonic endoscope deeply in the body cavity and may be advanced or returned.

According to the first embodiment, the radial tomographic image and the route tomographic image are arranged and displayed on the single monitor at the same time. However, both the images may be displayed on separate monitor and may be switched and displayed with the intersecting-line-segment marker.

According to the first embodiment, the transmitting coil 17 is arranged to the edge of the inserting portion 11 in the ultrasonic endoscope 2 and the receiving coils 32 are fixed in space. However, the reception and the transmission may be on the contrary.

According to the first embodiment, the position and the direction of the radial tomographic image are detected by using the magnetic field. However, they may be detected with the acceleration or another means.

Second Embodiment

The second embodiment is almost the same as the first embodiment, therefore, only different points are described, the same reference numerals denote the same components, and a description thereof is omitted.

Hereinbelow, a description is given of the structure and the operation of the ultrasonic diagnostic apparatus according to the second embodiment with reference to FIGS. 11 and 12.

(Structure)

Figure 11:
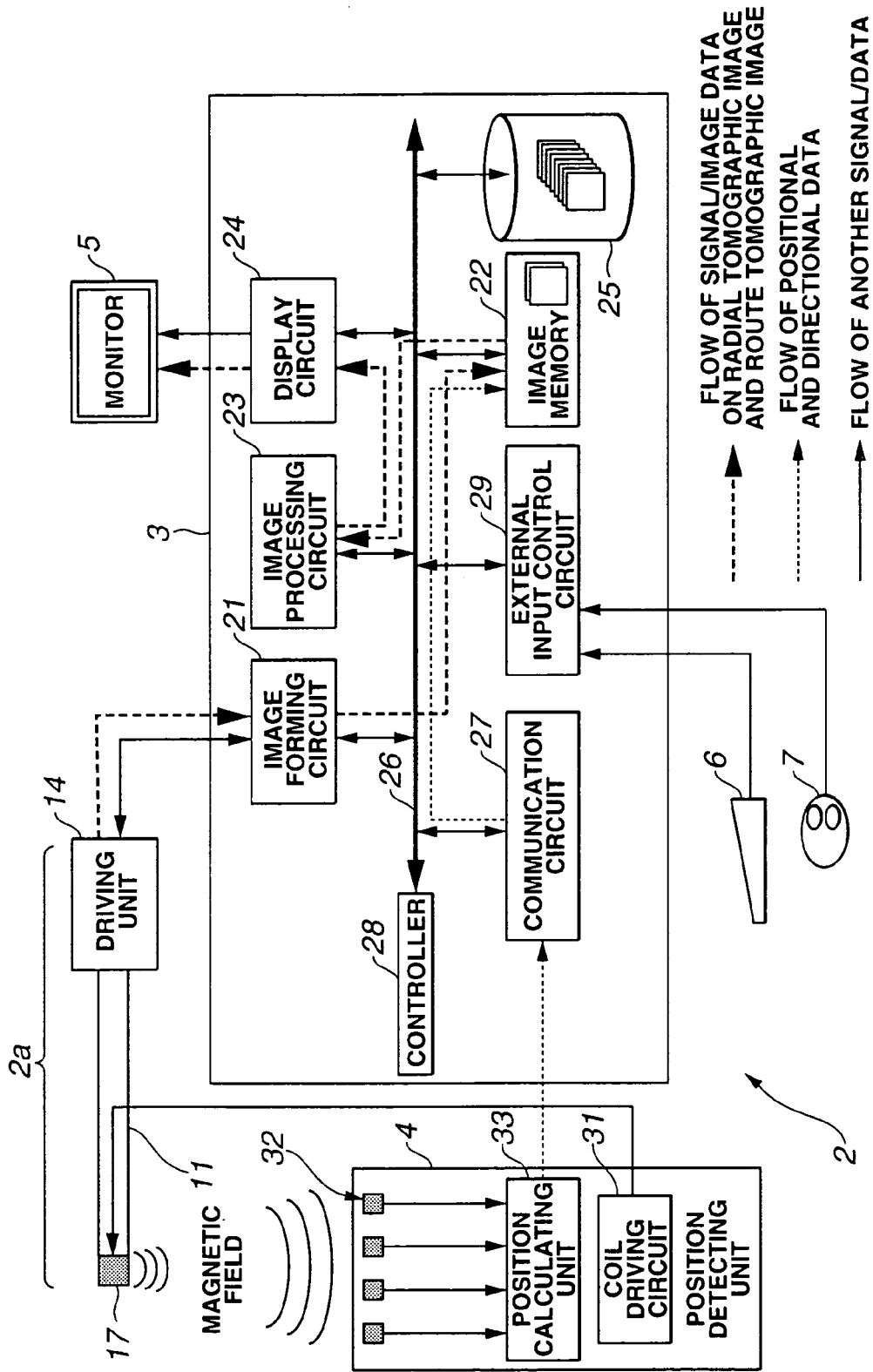
FIGS. 11 and 12 relate to the second embodiment of the present invention.

Referring to FIG. 11, the driving unit 14 according to the second embodiment does not have the motor. However, referring to FIG. 12, the ultrasonic vibrator is cut in rectangles at the edge of the inserting portion in an ultrasonic endoscope 2a according to the second embodiment and thus a circular array (hereinafter, referred to as an ultrasonic vibrator array) 51 is aligned around the inserting axis. Ultrasonic vibrators forming the ultrasonic vibrator array 51 are connected to the image forming circuit 21 in the ultrasonic observing unit 3 via the signal lines and the driving unit 14. Other structure is the same as that according to the first embodiment.

(Operation)

The operation for forming the radial tomographic image is different from that according to the first embodiment.

Among the ultrasonic vibrators forming the ultrasonic vibrator array 51, a part of and a plurality of the ultrasonic vibrators receive pulse excitation signals from the image forming circuit 21 in the ultrasonic observing unit 3, and convert the signals into ultrasonic waves as coarse waves of the medium. In this case, the image forming circuit 21 delays the excitation signals so that the excitation signals reach the ultrasonic vibrators at different times. This delay operation is implemented so that a single ultrasonic beam is formed when the ultrasonic waves excited by the ultrasonic vibrators are overlapped in the subject.

The ultrasonic beam is irradiated to the outside of the ultrasonic endoscope 2a, and the reflecting echo from the subject is returned to the ultrasonic vibrator while tracing the route contrary to that of the ultrasonic beam. The ultrasonic vibrators convert the reflecting echo into electric echo signals, and transmit the converted signals to the image forming circuit 21 via the route contrary to that of the excitation signals.

Figure 12:
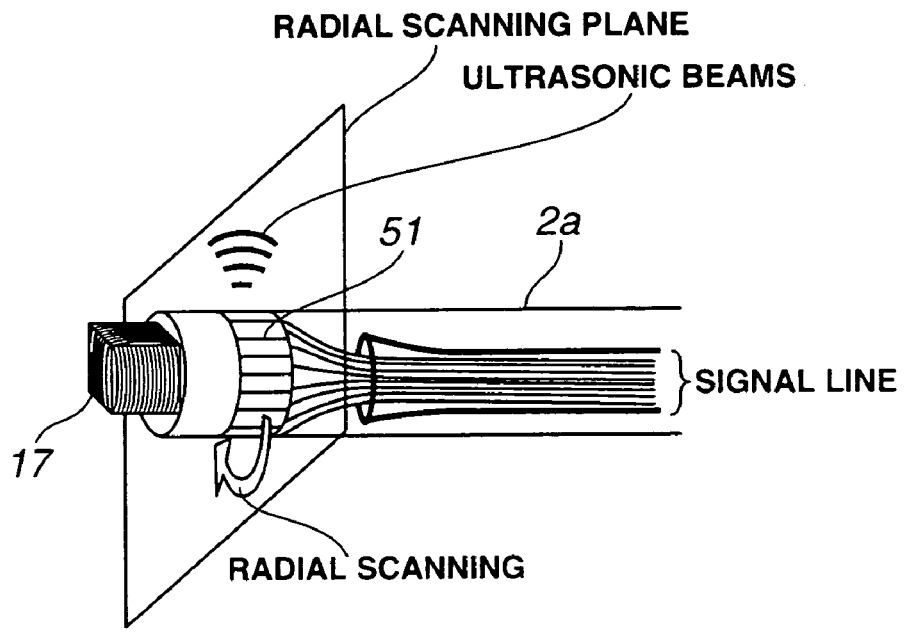

Next, the image forming circuit 21 selects again a plurality of ultrasonic vibrators for forming the ultrasonic beams and transmits the excitation signal so as to execute the radial scanning by the ultrasonic beams shown by an arrow in FIG. 12. Thus, the angle of the ultrasonic beams changes. By repeating the operation of the above image forming circuit 21, the so-called electric radial scanning is realized.

Other operations are the same as those according to the first embodiment.

(Advantages)

According to the first embodiment, the mechanical radial scanning is used and, therefore, the deviation of the flexible shaft 16 is caused and the deviations are not uniform among a plurality of radial tomographic images, thus resulting in the deviation on the route tomographic image. Because in the normal mechanical radial scanning, the angle and the position for the rotation of the motor 13 are detected by a rotary encoder adjacent to the motor 13.

However, according to the second embodiment, the electric radial scanning is used and, consequently, the above-mentioned problem of the deviation on the route tomographic image is solved. Other advantages are the same as those according to the first embodiment.

(Modification)

The radial scanning according to the second embodiment is implemented at the entire circumference with an angle of 360° or with an angle of 270° smaller than the foregoing.

Third Embodiment

The third embodiment is substantially the same as the first embodiment, therefore, only different points are described, the same reference numerals denotes the same components, and a description thereof is omitted.

(Structure and Operation)

Hereinbelow, the structure and the operation of an ultrasonic diagnostic apparatus will be described according to the third embodiment with reference to FIG. 13. The entire structural diagram is the same as FIG. 11.

Figure 13:
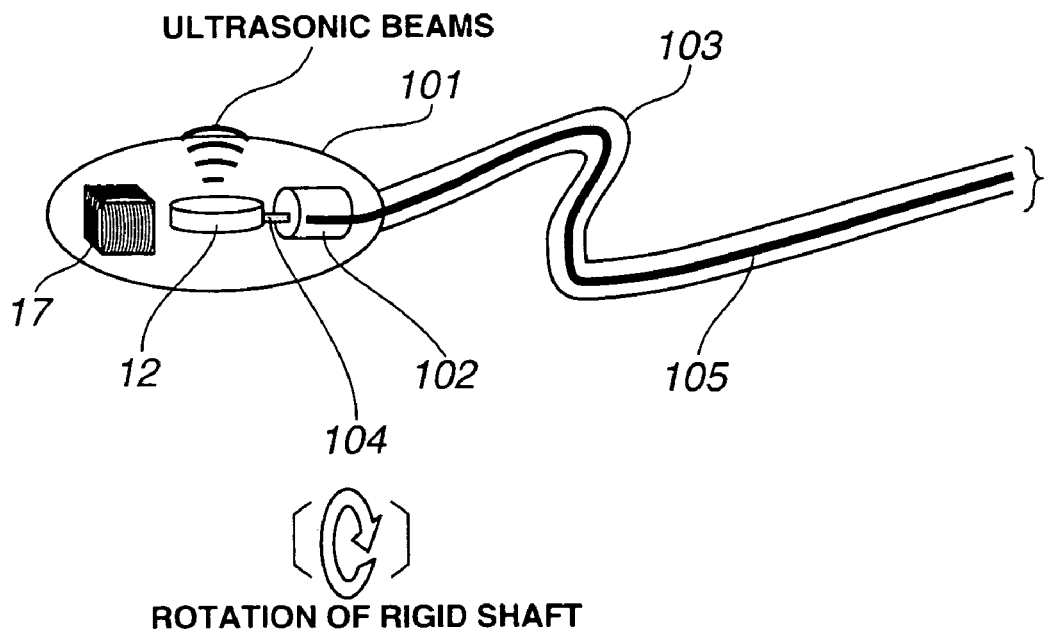
FIG. 13 is a structural diagram showing the structure of a capsule ultrasonic endoscope according to the third embodiment of the present invention.
Figure 14:
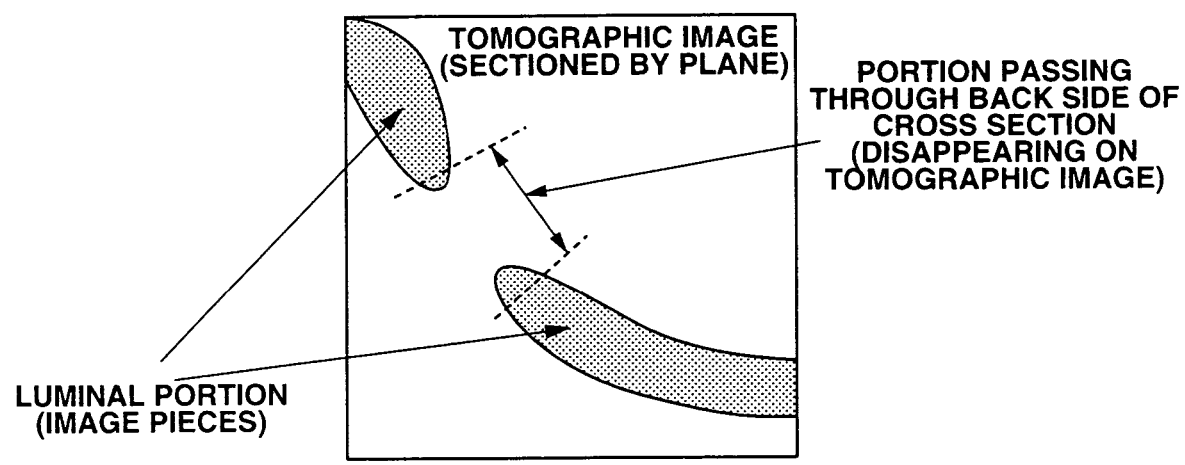
FIG. 14 shows a state of the luminal portion which partly runs on the depth side from the cross section.

Referring to FIG. 13, a radial scanning ultrasonic probe according to the third embodiment uses a capsule ultrasonic endoscope (hereinafter, referred to as the capsule ultrasonic endoscope) 101 as the radial scanning ultrasonic probe.

The capsule ultrasonic endoscope 101 comprises the transmitting coil 17, the ultrasonic vibrator 12, a rigid shaft 104, an ultracompact motor 102, and a signal cable 103. Unlike the first embodiment, the driving unit 14 does not have the motor 13. In place of the motor 13 in the driving unit 14, the capsule ultrasonic endoscope 101 has the ultracompact motor 102.

The ultrasonic vibrator 12 is connected to the rigid stick shaft 104. The rigid shaft 104 is connected to the ultracompact motor 102. The ultrasonic vibrator 12 is connected to the image forming circuit 21 in the ultrasonic observing unit 3 via the driving unit 13 and a signal line 105 passing though the rigid shaft 104, the ultracompact motor 102, and the signal cable 103. The transmitting coil 17 generates the magnetic field in space and is connected to the coil driving circuit 31 in the position detecting unit 4 via the signal line 105.

Other structure and operation are the same as those according to the first embodiment.

(Advantages)

According to the first embodiment, the deviations of the flexible shaft 16 are caused and the deviations are not uniform among the plurality of radial tomographic images, thus causing the problem of the deviation on the route tomographic image. Because, in the normal mechanical radial scanning, the angle and the position of the motor rotation are detected by the rotary encoder adjacent to the motor. However, according to the third embodiment, not the flexible shaft 16, but the ultracompact motor 102 and the rigid shaft 104 are arranged near the ultrasonic vibrator 12, thereby solving the problem.

Further, according to the third embodiment, the capsule ultrasonic endoscope 101 is used, thus, the examinee easily drinks the capsule, and the load thereof is reduced. Normally, the operator can not easily operate the radial scanning plane by using the capsule ultrasonic endoscope 101 and thus the observed portion of the subject is not easily recognized which part of the subject is observing. However, with the structure and the operation according to the third embodiment, the route tomographic image is observed and thus the operator easily performs the diagnosis.

Furthermore, since the observed portion is easily recognized which part of the subject is observing without the optical observing window, the components such as the optical observing window, the CCD camera, the glass fiber, and the video signal cable are not necessary and the capsule ultrasonic endoscope 101 is reduced in size.

In addition, normally, the capsule ultrasonic endoscope 101 cannot manually be advanced and returned. However, the route tomographic image is formed while the capsule ultrasonic endoscope 101 is advanced and returned by the natural swallowing, falling, and peristaltic motions, and thus the operator observes the images. Other advantages are the same as those according to the first embodiment.

According to the present invention, various embodiments can be implemented within the wide range of the present invention without departing from the spirit and the range thereof. The present invention is not limited by specific embodiments, except for the following claims.

INDUSTRIAL APPLICABILITY

As mentioned above, the ultrasonic diagnostic apparatus according to the present invention is advantageous as an apparatus for detecting the stretch of the observing portion in the luminal portion.

The invention claimed is:

1. An ultrasonic diagnostic apparatus which advances and returns a radial scanning ultrasonic vibrator in the living body of a subject and generates a plurality of time-series radial tomographic images in accordance with the advance and return, the ultrasonic diagnostic apparatus comprising:
   positional information detecting means which detects positional information of the radial scanning ultrasonic vibrator upon obtaining the radial tomographic image;
   a cross-sectional plane setting section which sets a cross-sectional plane for generating a route tomographic image of and along a route of the advance and return of the radial scanning ultrasonic vibrator; and
   route tomographic generating means which generates the route tomographic image on an image drawing plane which is parallel with the cross-sectional plane, based on the positional information obtained from the positional information detecting means and the plurality of the time-series radial tomographic images.

2. An ultrasonic diagnostic apparatus according to claim 1, further comprising:
   intersecting line segment extracting means which obtains an intersecting line segment between the radial tomographic image and each of a plurality of parallel planes passing through the center of the plurality of radial tomographic images,
   wherein the route tomographic image generating means generates the route tomographic image based on a plurality of intersecting line segments obtained by the intersecting line segment extracting means.

3. An ultrasonic diagnostic apparatus according to claim 2, wherein the intersecting line segment extracting means extracts the intersecting line segment every obtaining a new radial tomographic image, and
   the route tomographic image generating means generates the route tomographic image every extracting a new intersecting line segment.

4. An ultrasonic diagnostic apparatus according to claim 1, wherein the radial scanning ultrasonic probe is an electric radial scanning ultrasonic probe.

5. An ultrasonic diagnostic apparatus according to claim 1, wherein the radial scanning ultrasonic probe is arranged in a capsule inserted in the body cavity.

6. An ultrasonic diagnostic apparatus according to claim 5, wherein the capsule has a motor which rotates the ultrasonic vibrator.

7. An ultrasonic diagnostic apparatus which generates a new tomographic image based on a plurality of radial tomographic images obtained by an advancing and returning route of a radial scanning ultrasonic probe in the body cavity of a subject, the ultrasonic diagnostic apparatus comprising:
   positional and directional detecting means which detects positions and directions of the plurality of radial tomographic images;
   a cross-sectional plane setting section which sets a cross-sectional plane for generating a route tomographic image of and along a route of the advance and return of the radial scanning ultrasonic vibrator; and
   route tomographic image generating means which generates the route tomographic image on an image drawing plane which is parallel to the cross-sectional plane, based on the position and the direction.

8. An ultrasonic diagnostic apparatus according to claim 7, further comprising:
   intersecting line segment extracting means which obtains an intersecting line segment between the radial tomographic image and each of a plurality of parallel planes passing through the center of the plurality of radial tomographic images,
   wherein the route tomographic image generating means generates the route tomographic image based on a plurality of the intersecting line segments obtained by the intersecting line segment extracting means.

9. An ultrasonic diagnostic apparatus according to claim 8, wherein the intersecting line segment extracting means extracts the intersecting line segment every obtaining a new one of the radial tomographic images, and
   the route tomographic image generating means generates the route tomographic image every extracting a new intersecting line segment.

10. An ultrasonic diagnostic apparatus according to claim 9, further comprising:
    display means which comparably displays the radial tomographic image and the route tomographic image,
    wherein the display means superimposes and displays an intersecting-line-segment marker indicating the intersecting line segment on at least one of the radial tomographic image and the route tomographic image.

11. An ultrasonic diagnostic apparatus according to claim 10, further comprising:
    setting means which sets the position of the intersecting-line-segment marker,
    wherein the display means updates and displays the radial tomographic image or the route tomographic image in conjunction with the setting of the position of the intersecting-line-segment marker.

12. An ultrasonic diagnostic apparatus according to claim 10, wherein the intersecting line segment extracting means extracts the intersecting line segment between the already-formed route tomographic image and the radial scanning plane during the scanning, and
    the display means superimposes and displays the intersecting-line-segment marker indicating the intersecting line segment, as a guide of the radial scanning plane during the scanning, on the already-formed route tomographic image.

13. An ultrasonic diagnostic apparatus according to claim 8, further comprising:
    display means which comparably displays the radial tomographic image and the route tomographic image,
    wherein the display means superimposes and displays an intersecting-line-segment marker indicating the intersecting line segment on at least one of the radial tomographic image and the route tomographic image.

14. An ultrasonic diagnostic apparatus according to claim 13, further comprising:
    setting means which sets the position of the intersecting-line-segment marker, wherein the display means updates and displays the radial tomographic image or the route tomographic image in conjunction with the setting of the position of the intersecting-line-segment marker.

15. An ultrasonic diagnostic apparatus according to claim 13, wherein the intersecting line segment extracting means extracts the intersecting line segment between the already-formed route tomographic image and the radial scanning plane during the scanning, and the display means superimposes and displays the intersecting-line-segment marker indicating the intersecting line segment, as a guide of the radial scanning plane during the scanning, on the already-formed route tomographic image.

16. An ultrasonic diagnostic method for advancing and returning a radial scanning ultrasonic vibrator in the living body of a subject and generating a plurality of time-series radial tomographic images in accordance with the advance and return, the ultrasonic diagnostic method comprising:

a positional information detecting step of detecting positional information of the radial scanning ultrasonic vibrator upon obtaining the radial tomographic image;

a cross-sectional plane setting step of setting a cross-sectional plane for generating a route tomographic image of and along a route of the advance and return of the radial scanning ultrasonic vibrator; and a route tomographic generating step of generating the route tomographic image on an image drawing plane which is parallel with the cross-sectional plane, based on the positional information obtained by the positional information detecting step and the plurality of the time-series radial tomographic images.

17. An ultrasonic diagnosis method according to claim 16, wherein the radial scanning ultrasonic probe is an electric radial scanning ultrasonic probe.

18. An ultrasonic diagnostic method according to claim 16, wherein the radial scanning ultrasonic probe is arranged in a capsule inserted in the body cavity.

19. An ultrasonic diagnostic method according to claim 18, wherein the capsule has a motor which rotates the ultrasonic vibrator.

20. An ultrasonic diagnostic method for generating a new tomographic image based on a plurality of radial tomographic images obtained by an advancing and returning route of a radial scanning ultrasonic probe in the body cavity of a subject, the ultrasonic diagnosis method comprising:

a position and direction detecting step of detecting positions and directions of the plurality of radial tomographic images;

a cross-sectional plane setting step of setting a cross-sectional plane for generating a route tomographic image of and along a route of the advance and return of the radial scanning ultrasonic vibrator; and a route tomographic generating step of generating the route tomographic image on an image drawing plane which is parallel with the cross-sectional plane, based on the position and the direction.

* * * * *